(12) United States Patent
Wang et al.

(10) Patent No.: US 10,549,344 B2
(45) Date of Patent: Feb. 4, 2020

(54) LIQUID COMPOSITION

(71) Applicant: SHENMAO TECHNOLOGY INC., Taoyuan (TW)

(72) Inventors: Chang-Meng Wang, Taoyuan (TW); Hsiang-Chuan Chen, Taoyuan (TW); Ruei-Ying Sheng, Taoyuan (TW); Chen-Yi Chen, Taoyuan (TW); Albert T. Wu, Taoyuan (TW); Chih-Hao Chen, Taoyuan (TW); Yuan-Heng Zhong, Taoyuan (TW)

(73) Assignee: SHENMAO TECHNOLOGY INC., Taoyuan (TW)

( * ) Notice: Subject to any disclaimer, the term of this patent is extended or adjusted under 35 U.S.C. 154(b) by 249 days.

(21) Appl. No.: 15/798,510

(22) Filed: Oct. 31, 2017

(65) Prior Publication Data

US 2019/0054525 A1 Feb. 21, 2019

(30) Foreign Application Priority Data

Aug. 16, 2017 (TW) .............................. 106127696 A

(51) Int. Cl.
| | |
|---|---|
| B22F 1/00 | (2006.01) |
| B22F 3/10 | (2006.01) |
| B22F 3/12 | (2006.01) |
| C07C 55/02 | (2006.01) |
| C07C 55/22 | (2006.01) |
| C07D 307/62 | (2006.01) |
| C23C 24/10 | (2006.01) |
| B22F 7/04 | (2006.01) |

(52) U.S. Cl.
CPC .......... *B22F 1/0059* (2013.01); *B22F 3/1035* (2013.01); *B22F 3/1233* (2013.01); *C07C 55/02* (2013.01); *C07C 55/22* (2013.01); *C07D 307/62* (2013.01); *C23C 24/106* (2013.01); *B22F 2001/0066* (2013.01); *B22F 2007/047* (2013.01); *B22F 2301/10* (2013.01); *B22F 2302/45* (2013.01); *B22F 2304/058* (2013.01); *B22F 2304/10* (2013.01)

(58) Field of Classification Search
None
See application file for complete search history.

(56) References Cited

U.S. PATENT DOCUMENTS

| | | | | | |
|---|---|---|---|---|---|
| 4,039,697 | A | * | 8/1977 | Isawa ...................... | C23C 24/08 427/475 |
| 5,588,983 | A | * | 12/1996 | Tani .......................... | B22F 9/04 241/16 |
| 6,391,087 | B1 | * | 5/2002 | Hayashi ................. | B22F 1/0011 75/373 |
| 2006/0145125 | A1 | * | 7/2006 | Kuwajima ............... | H01B 1/22 252/500 |
| 2007/0209475 | A1 | * | 9/2007 | Sakaue .................. | B22F 1/0014 75/255 |
| 2008/0157029 | A1 | * | 7/2008 | Lee ........................ | B22F 1/0018 252/512 |
| 2009/0261304 | A1 | * | 10/2009 | Mori ...................... | B22F 1/0022 252/512 |
| 2010/0230644 | A1 | * | 9/2010 | Ryoshi .................. | B22F 1/0022 252/512 |
| 2013/0037747 | A1 | * | 2/2013 | Zhou .................... | C09K 11/7774 252/301.4 R |
| 2014/0216544 | A1 | * | 8/2014 | Nakahara .............. | H01L 31/048 136/256 |
| 2014/0367619 | A1 | * | 12/2014 | Summers ................. | H01B 1/22 252/512 |
| 2015/0079414 | A1 | * | 3/2015 | Kim .................... | C23C 18/1635 428/548 |
| 2015/0380123 | A1 | * | 12/2015 | Yatsuka ............... | H05K 3/1283 428/457 |

* cited by examiner

*Primary Examiner* — Joseph D Anthony
(74) *Attorney, Agent, or Firm* — Jackson IPG PLLC; Demian K. Jackson

(57) ABSTRACT

A liquid composition includes copper particles, an organic acid, and a solvent. The copper particle has a particle size of 0.5 μm~30 μm which falls in a micron scale. The liquid composition performs reaction sintering by redox reactions taken place between the copper particles and an organic acid solution at a low temperature of 150° C. in order to produce a dense copper layer and improve the conventional micron-scale copper particles that requires a protective atmosphere for the high-temperature sintering before achieving the required densification. This liquid composition also prevents an excessive oxidation of the nano copper particles during the low-temperature sintering process and a failure of the dense sintering. Due to the agglomeration of nano copper particles, some areas have to be sintered first, so that the sintered products have a good uniformity of tissue and a low resistance below 0.04 ohm per square (Ω/□).

6 Claims, No Drawings

LIQUID COMPOSITION

FIELD OF INVENTION

The present invention relates to a liquid composition formed by copper particles scattered in one or more types of organic acids, in particular to a liquid composition capable of carrying out reaction sintering at low temperature.

BACKGROUND OF INVENTION

1. Description of the Related Art

In metal sintering, metal particles is used as raw material and pressed by a mechanical force or any other external force to form a preform, and a target product such as a metal sintered body is formed by carrying out different sintering processes.

The conductivity and mechanical strength of the metal sintered body relate to the structural compactness of the metal sintered body, and the structural compactness comes from the benefit of sintering. Therefore, sintering is the core of the powder metallurgical process, and its effect is to remove pores between metal particles, so that the metal particles are consolidated in order to produce high-density products.

During sintering, the preform formed by pressing the metal particles is heated to a temperature greater than half of the absolute temperature of the melting point of the metal for densification.

In a conventional method, micron-scale metal particles are placed at high temperature for the densification of the metal particles to increase the mechanical strength after the preliminary molding, wherein such high temperature is lower than the temperature of the melting point of the metal particles. In the sintering process, the metal particles are prevented from being in contact with the oxygen gas in the atmosphere and from being oxidized, so that a reduced atmosphere or nitrogen gas is used to stop the metal particles from being oxidized excessively in the high temperature, so as to improve the sintering efficiency, compactness, and conductivity.

Most conventional nano metal sintering technologies use nanoscale metal particles as raw material for the sintering to produce micro workpieces or conductive wires with good electrical property and mechanical strength. At present, nano metal particles of silver or copper are used for the sintering of nano metals, wherein the total surface area of the nanoscale particles and the total surface of the products can be increased significantly to lower the sintering temperature of the nanoparticles, and this sintering method is the low temperature sintering method.

In general, the sintering temperature for the sintering process that uses nano silver or copper particles is approximately 200° C. Although the nano metal particles can have a reaction sintering at the sintering temperature of approximately 200° C., yet the total surface area of the nano metal particles is increased significantly, so that the nano metal particles may be agglomerated easily. In addition, the nano metal particles may be oxidized during the sintering process, so that the sintered product may have non-uniform density and high porosity, and the electrical, thermal, and mechanical characteristics of the product are not as good as the original expected values.

In prior arts, nano copper particles have good electrical property without any risk of electromigration, and thus catching special attention. Although nano copper particles can be sintered at low temperature, the surface area of the nano copper particles is large, and the oxidation level of nano copper particles is also high, so that the sintered products have poor densification, and low conductivity. Furthermore, the nano copper particles are scattered into a solution and agglomerated easily, therefore the scatterability of the nano copper particles in the solution cannot be controlled, and an electrically conductive layer with stable quality, high uniformity of tissue, and or good sintering cannot be formed easily.

2. Summary of the Invention

In view of the aforementioned drawbacks of the prior art, it is a primary objective of the present invention to provide a liquid composition, particularly the liquid composition formed by micron-scale copper particles scattered in one or more types of organic acids and provided specifically for performing reaction sintering at low temperature to overcome the drawback of the micron-scale metal particles requiring high temperature and long time for the sintering, and requiring a reducing atmosphere or protective atmosphere. The liquid composition of the present invention also prevents the excessive oxidation of the nano metal particles occurred at the low-temperature sintering process, and the liquid composition formed by the micron-scale copper particles the present invention is capable of carrying out the reaction sintering at low temperature without having any excessive oxidation of the copper particles, and the sintered products have good conductivity and low resistance below 0.04 ohm per square ($\Omega/\square$).

To achieve the aforementioned and other objectives, the present invention provides a liquid composition capable of performing a reaction sintering at low temperature, and the low temperature refers to a temperature below 150° C., and a redox reaction is taken place between the copper particles and the organic acid solution, wherein a part of the surface of the copper particle is dissolved into the organic acid solution to form copper ions, and then the liquid composition is applied to a substrate, and then the copper ions are reduced back to the copper particles, so as to promote the original copper particles to perform the low-temperature sintering and form a dense and uniform copper layer in the low-temperature reaction sintering process.

To achieve the aforementioned and other objectives, the present invention provides a liquid composition, a plurality of copper particles, an organic acid and a solvent, characterized in that the plurality of copper particles has a particle size falling within a range of 0.5 μm~30 μm; the organic acid is at least one selected from the group consisting of a saturated organic acid, an oxalic acid, an ascorbic acid, a citric acid, an oleic acid, a linoleic acid, an α linoleic acid, a stearic acid, a tartaric acid, a benzoic acid, a phthalic acid, an acrylic acid and a methacrylic acid; and the solvent is at least one selected from the group consisting of free water, methanol, ethanol, isopropanol and butanol.

Wherein, the organic acid contains the ascorbic acid and at least one selected from the group consisting of a saturated organic acid, an oxalic acid, a citric acid, an oleic acid, a linoleic acid, an α linoleic acid, a stearic acid, a tartaric acid, a benzoic acid, a phthalic acid, an acrylic acid and a methacrylic acid.

Wherein, the organic acid has a concentration of 0.01M~5M.

Wherein, the copper particle has a concentration of 0.01M~5M.

Wherein, the organic acid comprises the ascorbic acid, the oxalic acid, and at least one selected from the group consisting of saturated organic acid, citric acid, oleic acid, linoleic acid, α linoleic acid, stearic acid, tartaric acid, benzoic acid, phthalic acid, acrylic acid and methacrylic acid.

Wherein, the organic acid is the ascorbic acid containing 1 wt %~30 wt % of the total of the organic acid.

Wherein, the organic acid is the oxalic acid containing 1 wt %~10 wt % of the total of the organic acid.

Wherein, the liquid composition further comprises an additive selected from the group consisting of free gelatin, agar and silicone.

Wherein, the additive is gelatin.

Wherein, the gelatin has a concentration of 0.01M~1M.

The liquid composition of the present invention capable of performing a reaction sintering at low temperature comprises an organic acid solution formed by copper particles, an organic acid, and a solvent. Wherein, the copper particle has a particle size falling within a range of 0.5 μm~30 μm, and a molar concentration of 0.01~5 with respect to the whole liquid composition. The organic acid solution may be formed by mixing one or more types of organic acids and has a molar concentration of 0.01~5 with respect to the whole solution. The liquid composition is coated onto a glass or copper foil substrate, and placed in an oven or heated by a hot plate, and a reaction sintering is taken place at a temperature below 150° C., and a dense conductive structural layer with strong adhesiveness and on low resistance below 0.04 ohm per square ($\Omega/\square$) is formed on a glass or copper foil substrate.

In the liquid composition, an additive is added, and a conductive structural layer is formed on the glass or copper foil substrate according to the aforementioned method. A metal complex may be formed by the additive and the copper ions in the liquid composition and provided for maintaining the stability of the liquid composition and increasing the concentration of the copper ions as a result of the colloidization of the additive and the vaporization of the solvent occurred in the heating environment, so that the copper particles have the reaction sintering to improve the sintering efficiency and the structural compactness.

BRIEF DESCRIPTION OF THE DRAWINGS

Nil

DESCRIPTION OF THE PREFERRED EMBODIMENTS

The above and other objects, features and advantages of this disclosure will become apparent from the following detailed description taken with the accompanying drawings. It is noteworthy that the embodiments are provided for illustrating the present invention, but not intended for limiting the scope of the invention. In addition, the symbol "~" used in this specification and claims of the present invention refers to a range of numerical values between a lower limit and an upper limit; "wt %" refers to percentage by weight, "M" refers to the molar concentration by volume, and hereinafter referring to as "molar concentration" with a unit of mol/L; "particle size" refers to the particle size measured by a laser particle size analyzer.

The present invention provides a liquid composition capable of performing reaction sintering at low temperature, and particularly a liquid composition capable of performing the reaction sintering at 150° C. The liquid composition of the present invention comprises a plurality of copper particles, at least one organic acid, and a solvent.

The copper particle is at least one selected from the group consisting of pure copper particle and copper particle with copper oxide on its surface, and the particle size falls within a range of 0.5 μm~30 μm, which is in a micron scale. As to the whole liquid composition, the concentration of copper particles is 0.015 molar concentration. The aforementioned pure copper particle is formed by un-oxidized copper metal. In a preferred embodiment of the present invention, the copper particle refers to a copper particle having copper oxide on its surfaces. For example, the whole copper particle is formed by copper oxide, or the copper particle has a core made of pure copper and an outer surface made of copper oxide.

The organic acid is formed by mixing one or more types of organic acids according to a proportion, and the organic acid is one selected from the group consisting of saturated organic acid, oxalic acid, ascorbic acid, citric acid, oleic acid, linoleic acid, α linoleic acid, stearic acid, tartaric acid, benzoic acid, phthalic acid, acrylic acid and methacrylic acid, and preferably formed by mixing 1 wt %~30 wt % of ascorbic acid, 1 wt %~10 wt % of oxalic acid and other mixed acid. Compared with the whole liquid composition, the organic acid has a concentration of 0.015 molar concentration.

The solvent is at least one selected from the group consisting of free water, methanol, ethanol, isopropanol and butanol.

To improve the sintering efficiency and structural compactness, the liquid composition further comprises an additive such as a dispersant capable of dispersing the copper particles in the liquid composition uniformly, and the additive is at least one selected from the group consisting of free gelatin, agar and silicone and has a molar concentration of 0.01~1 and preferably a molar concentration of 0.05 with respect to the whole solution.

The preparation of the liquid composition in accordance with the present invention is described as follows.

The method for manufacturing the liquid composition of the present invention comprises the following steps: (1) Prepare different organic acids according to a predetermined wt % and mix the organic acids with a solvent to form an organic acid solution with a predetermined molar concentration; (2) Uniformly mix the copper particles with the corresponding particle size and weight with the prepared organic acid solution uniformly at room temperature, and selectively add an appropriate additive to complete producing the liquid composition.

The preparation of the metal copper layer in accordance with the present invention is described as follows.

Coat the liquid composition on a glass plate to form a square plate with a side of 1 cm by a screen printing method, and dry the glass plate in oven at a predetermined temperature for a predetermine time and perform reaction sintering of a copper layer in form of a sheet. Test the thickness of the copper layer (140 μm) after the sintering process.

Electrical Measurement

A four-point probe measurement method is used for measuring the sheet resistance of the aforementioned copper layer, and an average measurement of the sheet resistance of five points is recorded, and the standard deviation of the sheet resistance of the five points is calculated. The lower the sheet resistance, the better the conductivity of the copper layer. The lower the standard deviation, the higher sintering structural compactness of the copper layer, and the better the sintering effect.

The copper particle has a particle size falling within a range of 0.5 μm~30 μm.

To study the relation between the particle size of the metal copper particle and the sintering effect, the liquid composition prepared according to the present invention and the metal copper layer manufactured by the method of the invention are used to produce different copper layers as listed in Table 1. Table 1 includes Embodiments 1~4 and Comparative Example 1 for comparing the embodiments, and a laser particle size analyzer is provided for measuring the particle size of the copper particle and selects the copper particles with the particle sizes of 0.5~30 μm, 0.5~10 μm, 0.5~5 μm and 0.5~3 μm for Embodiments 1 to Embodiment 4 respectively, and Comparative Examples 1 selects the copper particles with a particle size of 0.5~60 μm. The copper particles in the liquid composition are prepared with a molar concentration of 1M. Wherein, the organic acid in the organic acid solution is ascorbic acid, and the ascorbic acid has a molar concentration of 1M with respect to the liquid composition, and the solvent is water. The copper particles, acid, and water are mixed uniformly at room temperature to form the liquid composition, and then the liquid composition is coated onto the glass plate, and then the glass plate is put into an over at 100° C. for 30 minutes for the reaction sintering. In addition, the electrical measurement method of the present invention is used to measure the sheet resistance in Embodiments 1~4 and Comparative Example 1 and the results are listed below:

TABLE 1

| Liquid composition No. | Particle Size of Copper Particle (μm) | Sheet Resistance of Copper Layer (Ω/□) | Standard Deviation of Sheet Resistance (Ω/□) |
| --- | --- | --- | --- |
| Embodiment 1 | 0.5~30 | 0.0124 | 0.031 |
| Embodiment 2 | 0.5~10 | 0.0118 | 0.024 |
| Embodiment 3 | 0.5~5 | 0.0107 | 0.020 |
| Embodiment 4 | 0.5~3 | 0.0102 | 0.019 |
| Comparative Example 1 | 0.5~60 | 0.0467 | 0.192 |

In Table 1, the range of selecting the particle size of the copper particle will affect the sheet resistance and standard deviation of the copper layer. In Comparative Example 1, the copper particle with a particle size falling within a range of 0.5~60 μm is selected, but the range of the particle sizes is too broad, so that the sintering effect will be poor and the sintering structure is loose, and the sheet resistance will exceed 0.04Ω/□ and the conductivity will be unqualified. In Embodiments 1~4, the copper particles with a particle size falling within a range of 0.530 μm are used to obtain a good electrical property and a sheet resistance smaller than 0.04Ω/□, and it shows that using the copper particles with such particle size can manufacture a liquid composition to obtain the copper layer with a high compactness and a micro sintering structure; and using the copper particles with a particle size falling within the range of 0.530 μm can obtain a standard deviation of the sheet resistance which is smaller than 0.1Ω/□. It shows that using the copper particles with a particle size of such range can prepare a liquid composition and the copper layer of a high uniformity and a micro sintering structure.

In the following embodiments and comparative examples, the copper particles having a particle size falling within a range of 0.5 μm~30 μm are selected and mixed with an organic acid solution with different concentrations of the organic acid in the embodiments and comparative examples.

Ascorbic Acid of 1 wt %~30 wt %:

To study the relation between the types of organic acids and the sintering effect, the liquid composition is prepared and the metal copper layer is manufactured according to the present invention, and different copper layers are listed in Table 2. Table 2 includes Embodiments 5~9 of the present invention and Comparative Example 2 for comparing with the embodiments, and the copper particle with a particle size falling within a range of 0.5 μm~30 is selected; and the copper particles are manufactured with a molar concentration 1M with respect to the liquid composition. Wherein, the organic acid in the organic acid solution is a mixture with the following contents: ascorbic acid and at least one selected from the group consisting of saturated organic acid, oxalic acid, citric acid, oleic acid, linoleic acid, α linoleic acid, stearic acid, tartaric acid, benzoic acid, phthalic acid, acrylic acid and methacrylic acid, and the whole organic acid in the liquid composition has a molar concentration of 1M, and the solvent is water, and the acids and solvent are mixed uniformly at room temperature to form the liquid composition, and then the liquid composition is coated onto the glass plate, and then the glass plate is put into an oven at 100° C. oven for 30 minutes for reaction sintering. The electrical measurement method of the present invention is used to measure the sheet resistance in Embodiments 5~9 and Comparative Example 2.

TABLE 2

| Liquid composition No. | Ascorbic Acid (wt %) | Other Mixed Organic Acid (wt %) | Sheet Resistance of Copper Layer (Ω/□) |
| --- | --- | --- | --- |
| Embodiment 5 | 1 | Balance | 0.0239 |
| Embodiment 6 | 10 | Balance | 0.0137 |
| Embodiment 7 | 15 | Balance | 0.0149 |
| Embodiment 8 | 20 | Balance | 0.0174 |
| Embodiment 9 | 30 | Balance | 0.0231 |
| Comparative Example 2 | 35 | Balance | 0.0633 |

The term "Balance" should be interpreted as it is for the organic acid, and the organic acid has a content supplemented to the 100 wt % and formed by mixing other organic acids. In Embodiments 5~9 and Comparative Example 2 of the present invention, the organic acid is formed by ascorbic acids with different weight percentages and used for study the sintering structure. In the result as shown in Table 2, the liquid composition uses the ascorbic acid of 1 wt %~30 wt % according to Embodiments 5~9 to obtain a sheet resistance falling within a range of 0.0137Ω/□~0.0239Ω/□ which is smaller than 0.04Ω/□, and the copper layer with a good electrical property and a good sintering structure. If the liquid composition uses the ascorbic acid of 35 wt % according to Comparative Example 2 to produce the copper layer with a sheet resistance of 0.0633Ω/□ which is greater than 0.04Ω/□ and an unqualified electrical property.

Ascorbic Acid of 1 wt %~30 wt % and Oxalic Acid of 1 wt %~10 wt %:

To study the relation between the types of organic acids and the sintering effect, the liquid composition prepared and the metal copper layer manufactured according to the present invention are listed in Table 3. Table 3 includes Embodiments 10~15 of the present invention and Comparative Example 3 for comparing the embodiments, and the copper particles with a particle size falling within a range of 0.5 μm~30 μm are used, and the copper particles in the liquid composition are prepared with a molar concentration of 1M.

Wherein, the organic acid in the organic acid solution is a mixture of ascorbic acid, oxalic acid and at least one selected from the group consisting of saturated organic acid, citric acid, oleic acid, linoleic acid, α linoleic acid, stearic acid, tartaric acid, benzoic acid, phthalic acid, acrylic acid and methacrylic acid, and the whole organic acid in the liquid composition has a molar concentration of 1M, and the solvent is water, and the organic acids and water are mixed uniformly at room temperature to form the liquid composition, and then the liquid composition is coated onto the glass plate, and the glass plate is put into an oven at 100° C. oven for 30 minutes for reaction sintering. In addition, the electrical measurement method of the present invention is used to measure the sheet resistance in Embodiments 10~15 and Comparative Example 3.

TABLE 3

| Liquid composition No. | Ascorbic Acid (wt %) | Oxalic Acid (wt %) | Other Mixed Organic Acid (wt %) | Sheet Resistance of Copper Layer ($\Omega/\square$) |
|---|---|---|---|---|
| Embodiment 10 | 1 | 1 | Balance | 0.0251 |
| Embodiment 11 | 1 | 5 | Balance | 0.0214 |
| Embodiment 12 | 1 | 10 | Balance | 0.0142 |
| Embodiment 13 | 30 | 1 | Balance | 0.0188 |
| Embodiment 14 | 30 | 5 | Balance | 0.0169 |
| Embodiment 15 | 30 | 10 | Balance | 0.0237 |
| Comparative Example 3 | 35 | 12 | Balance | 0.0402 |

The term "Balance" should be interpreted as it is for the organic acid, and the organic acid has a content supplemented to the 100 wt % and formed by mixing other organic acids. In Embodiments 10~15 and Comparative Example 3 of the present invention, the organic acid is formed by ascorbic acid of 1 wt %~30 wt % and oxalic acid of 1 wt %~10 wt % and used for study the sintering structure. In the result as shown in Table 3, the liquid composition uses the ascorbic acid of 1 wt % and the oxalic acid of 1 wt %~10 wt % according to Embodiments 10~12 to obtain a copper layer with a sheet resistance falling within a range of 0.0142$\Omega$/$\square$~0.0251$\Omega$/$\square$, and the liquid composition uses the ascorbic acid of 30 wt % and the oxalic acid of 1 wt %~10 wt % according to Embodiments 13~15 to obtain a copper layer with a sheet resistance of 0.0169$\Omega$/$\square$~0.0237$\Omega$/$\square$, and both sheet resistances are smaller than 0.04$\Omega$/$\square$ and both have the copper layers with a good electrical property, and it indicates a good sintering structure. If the liquid composition uses an ascorbic acid greater than 30 wt % and an oxalic acid greater than 10 wt %, such as Comparative Example 3 using 35 wt % of ascorbic acid and 12 wt % of oxalic acid to produce a sheet resistance of 0.0402$\Omega$/$\square$, the copper layer with the sheet resistance greater than 0.04$\Omega$/$\square$ has an unqualified electrical property.

To study the relation between the molar concentration of the copper particle and the additive and the sintering effect, different copper layers of the liquid composition prepared according to the preparation of the liquid composition and the manufacturing method of the metal copper layer in accordance with the present invention are listed in Table 4 below. Table 4 includes Embodiments 16~23 of the present invention and Comparative Examples 4~7 for comparing with the embodiments, and the copper particle has a particle size of 0.5 μm~30 μm, and the copper particles are manufactured with a molar concentration with respect to the whole liquid composition as listed in Table 4. Wherein, the organic acid in the organic acid solution is a mixture with the following contents: 30 wt % of ascorbic acid, 10 wt % of oxalic acid, and 60 wt % of other organic acids, and the organic acid of the whole 100 wt % is prepared with a molar concentration with respect to the liquid composition as listed in Table 4. In Table 4, the additive used is gelatin with a concentration as listed in Table 4, and the solvent is water. At room temperature, the organic acids are mixed uniformly to form the liquid composition, and then the liquid composition is coated onto the glass plate, and then the mixture is put into an oven at different sintering temperatures as listed in Table 4 for reaction sintering for 30 minutes. In addition, the electrical measurement method of the present invention is used to measure the sheet resistance in Embodiments 16~23 and Comparative Examples 4~7 and the calculation of the standard deviation of the sheet resistance.

TABLE 4

| Liquid composition No. | CCP (M) | COA (M) | CA (M) | Sintering Temperature (° C.) | Sheet Resistance of Copper Layer ($\Omega/\square$) | Standard Deviation of Sheet Resistance ($\Omega/\square$) |
|---|---|---|---|---|---|---|
| Embodiment 16 | 0.01 | 5 | 0 | 25 | 0.0244 | 0.065 |
| Embodiment 17 | 0.01 | 5 | 0 | 100 | 0.0122 | 0.027 |
| Embodiment 18 | 0.01 | 5 | 0 | 150 | 0.0153 | 0.034 |
| Embodiment 19 | 0.01 | 5 | 0.05 | 100 | 0.0095 | 0.020 |
| Embodiment 20 | 5 | 0.01 | 0 | 25 | 0.0220 | 0.057 |
| Embodiment 21 | 5 | 0.01 | 0 | 100 | 0.0113 | 0.022 |
| Embodiment 22 | 5 | 0.01 | 0 | 150 | 0.0125 | 0.034 |
| Embodiment 23 | 5 | 0.01 | 0.05 | 100 | 0.0084 | 0.013 |
| Comparative Example 4 | 0.01 | 5.5 | 0.05 | 100 | 0.0867 | 0.209 |
| Comparative Example 5 | 5.5 | 0.01 | 0.05 | 100 | 0.0747 | 0.152 |
| Comparative Example 6 | 0.01 | 5 | 0.05 | 200 | 0.0894 | 0.286 |
| Comparative Example 7 | 5 | 0.01 | 0.05 | 200 | 0.0928 | 0.296 |

CCP: Concentration of Copper Particle;
COA: Concentration of Organic Acid;
CA: Concentration of Additive.

The copper particle has a molar concentration of 0.01M~5M, and the organic acid has a concentration of 0.01M~5M.

In Table 4, Embodiments 16~18 use the copper particles with a molar concentration of 0.01M, and the organic acid has a concentration of 5M; Embodiments 20~22 use the copper particles with a molar concentration of 5M, and the organic acid has a concentration of 0.01M; Embodiments 16~18 and Embodiments 20~22 show that the sheet resistance of each copper layer is smaller than 0.04$\Omega$/$\square$ and have a good electrical property. This result shows that copper particles with a molar concentration of 0.01M~5M and the organic acid with a concentration of 0.01M~5M can be used to prepare the liquid composition with high compactness and the copper layer with a micro sintering structure, and copper particles with a molar concentration of 0.01M~5M and the organic acid with a concentration of 0.01M~5M can be used to prepare the liquid composition with a standard deviation of the sheet resistance smaller than 0.1$\Omega$/$\square$. It shows that the copper particles with a molar concentration of 0.01M~5M and the organic acid with a concentration of 0.01M~5M can be used to prepare the liquid composition with high uniformity and the copper layer with a micro sintering structure.

The difference between Embodiment 19 and Comparative Example 4 resides on that the organic acid in the liquid composition of Embodiment 19 has a molar concentration of 5M, and the organic acid of Comparative Example 4 has a molar concentration of 5.5M. Obviously, the sheet resistance of 0.0095Ω/□ of the copper layer (lower than 0.04Ω/□, which is qualified) when the organic acid has a molar concentration of 5M in Embodiment 19 is increased to the sheet resistance of 0.0867Ω/□ (higher than 0.04Ω/□, which is unqualified) when the organic acid has a molar concentration of 5.5M in Comparative Example 4, and the standard deviation of the sheet resistance of 0.020Ω/□ of the copper layer (lower than 0.1Ω/□, which is qualified) when the organic acid has a molar concentration of 5M in Embodiment 19 is increased to the sheet resistance of 0.209Ω/□ of the copper layer (higher than 0.1Ω/□, which is unqualified) when the organic acid has a molar concentration of 5.5M in Comparative Example 4. Since too much organic acid is added into the liquid composition of Comparative Example 4, gaps are formed in the copper layer in the reaction sintering process due to the incomplete reaction sintering, and thus the compactness of the copper layer is poor and the uniformity of the copper layer is low. Similarly, the difference between Embodiment 23 and Comparative Example 5 resides on that the copper particle in the liquid composition of Embodiment 23 has a molar concentration of 5M, and the copper particle of Comparative Example 5 has a molar concentration of 5.5M. Obviously, the sheet resistance 0.0084Ω/□ of the copper layer (lower than 0.04Ω/□, which is qualified) when the copper particle has a molar concentration of 5M) in Embodiment 23 is increased to 0.0747Ω/□ (higher than 0.04Ω/□, which is unqualified) when the copper particle has a molar concentration of 5.5M in Comparative Example 5, and the standard deviation of the sheet resistance 0.013Ω/□ of the copper layer (lower than 0.1Ω/□, which is qualified) when the copper particle has a molar concentration of 5M in Embodiment 23 is increased to 0.152Ω/□ (higher than 0.1Ω/□, which is unqualified) when the copper particle has a molar concentration of 5.5M in Comparative Example 5. Since too many copper particles are added into the liquid composition of Comparative Example 5, the copper particles in the liquid composition are dispersed non-uniformly, so that the uppermost layer of the copper layer has non-reacted copper particles agglomerated with each other, so that the cooper layer formed in the reaction sintering process has poor compactness and low uniformity.

The additive has a molar concentration of 0.01M~1M.

Table 4 shows that Embodiments 17 and 19 use the copper particles with the same molar concentration of 0.01M, and the organic acid with a concentration of 5M, and their difference resides on that the liquid composition of Embodiment 19 further adds a gelatin with a molar concentration of 0.05M as an additive, wherein the gelatin has the effect of the dispersant. Obviously, the sheet resistance of the copper layer without any additive is dropped from 0.0122Ω/□ in Embodiment 17 to 0.0095Ω/□ in Embodiment 19, and the standard deviation of the sheet resistance of the copper layer is dropped from 0.027Ω/□ in Embodiment 17 to 0.020Ω/□ in Embodiment 19. Since the liquid composition is added with the additive, the copper particles can be dispersed uniformly in the liquid composition, and the copper layer has a micro sintering structure with high compactness and uniformity. Similarly, Embodiments 21 and Embodiment 23 use the copper particles with the same molar concentration of 5M and the organic acid with a concentration of 0.01M, and their difference resides on that the liquid composition of Embodiment 23 further adds a gelatin with a molar concentration of 0.05M as the additive, and the gelatin has the effect of a dispersant. Obviously, the sheet resistance of the copper layer without the additive according to Embodiment 21 is dropped from 0.0113Ω/□ to 0.0084Ω/□ in Embodiment 23, and the standard deviation of the sheet resistance of the copper layer is dropped from 0.022Ω/□ according to Embodiment 21 to 0.013Ω/□ according to Embodiment 23. Since the liquid composition is added with the additive, the copper particles can be dispersed uniformly in the liquid composition, and the copper layer has a micro sintering structure with high compactness and uniformity. In addition, the additive will be colloidized in the heating process, so that the copper ions carrying a positive charge will be reduced back to the original copper particles in the reaction sintering process, and the additive carrying a negative charge will be reacted continuously with other surrounding copper ions carrying the positive charge, so as to improve the chance of the occurrence of the reaction sintering. In the heating process, the solvent is vaporized, and the additive is colloidized, so that the concentration of copper ions will be increased, and the reduction efficiency will be increased to improve the compactness of the sintering structure. Therefore, a sintering structure with uniform and structural compactness will be obtained, and the copper layer has a good electrical property.

The reaction sintering temperature may be lower than 150° C.

The difference between Embodiment 19 and Comparative Example 6 resides on that the reaction sintering temperature of the liquid composition in Embodiment 19 is 100° C. and the reaction sintering temperature of Comparative Example 6 is 200° C. Obviously, the sheet resistance of the copper layer is increased from 0.0095Ω/□ (lower than 0.04Ω/□, which is qualified) in Embodiment 19 having a reaction sintering temperature of 100° C. to 0.0894Ω/□ (higher than 0.04Ω/□, which is unqualified) in Comparative Example 6 having a reaction sintering temperature of 200° C., and the standard deviation of the sheet resistance of the copper layer is increased from 0.020Ω/□(lower than 0.1Ω/□, which is qualified) in Embodiment 19 having a reaction sintering temperature of 100° C. to 0.286Ω/□ (higher than 0.1Ω/□, which is unqualified) in Comparative Example 6 having a reaction sintering temperature of 200° C. Since the reaction sintering temperature of the liquid composition of Comparative Example 6 is increased to 200° C., the copper particle and the organic acid solution will be reacted too quickly to produce larger groups of copper particles due to the agglomeration of the copper particles which are unfavorable to the uniform sintering. As a result, the density of the copper particles will be non-uniform, the quantity of gaps so formed will be increased, the sheet resistance will be increased, and a good electrical property will not be achieved. Similarly, Embodiment 23 and Comparative Example 7 also show a similar temperature effect, and thus will not be repeated. In the comparison of different reaction sintering temperatures, the reaction sintering temperature of Embodiments 18 and 22 is 150° C., and the reaction sintering temperature of Embodiment 16 and Embodiment 20 is 25° C., and both temperature can be used to produce a micro sintering structure with high compactness and uniformity, and the sheet resistances of different copper layers are lower than 0.04Ω/□ and the standard deviations of the sheet resistance are lower than 0.1Ω/□, and these results show that such copper layers have a good electrical property. In the present invention, Embodiment 23 is a preferred embodiment.

In summation, the present invention provides a liquid composition capable of performing a reaction sintering at low temperature and uses the liquid composition to perform the reaction sintering at low temperature without having any excessive oxidation of the copper particles or any agglomeration of copper particles, so that the sintered products have uniform and compact tissues and good conductivity, and the sintered conductive structural layer may be applied in the soldering of an electric distribution layer, an electrode, or a micro electronic component, and thus the invention is very useful for industrial application.

What is claimed is:

1. A liquid composition, comprising: a plurality of copper particles, an organic acid and a solvent, characterized in that the plurality of copper particles has a particle size falling within a range of 0.5 μm~30 μm; the organic acid comprises an ascorbic acid, an oxalic acid, and at least one selected from the group consisting of a saturated organic acid, a citric acid, an oleic acid, a linoleic acid, an α linoleic acid, a stearic acid, a tartaric acid, a benzoic acid, a phthalic acid and an acrylic acid; and the solvent is at least one selected from the group consisting of free water, methanol, ethanol, isopropanol and butanol; wherein the organic acid has a concentration of 0.01M~5M and the copper particle has a concentration of 0.01M~5M.

2. The liquid composition of claim 1, wherein the organic acid is the ascorbic acid containing 1 wt %~30 wt % of the total of the organic acid.

3. The liquid composition of claim 2, wherein the organic acid is the oxalic acid containing 1 wt %~10 wt % of the total of the organic acid.

4. The liquid composition of claim 3, further comprising an additive selected from the group consisting of free gelatin, agar and silicone.

5. The liquid composition of claim 4, wherein the additive is gelatin.

6. The liquid composition of claim 5 wherein the gelatin has a concentration of 0.01M~1M.

* * * * *